United States Patent
Shukla et al.

(12)

(10) Patent No.: US 6,320,030 B1
(45) Date of Patent: Nov. 20, 2001

(54) MUCIN-BIOMOLECULES COMPLEX FOR TRANSFECTION

(76) Inventors: Ashok K Shukla; Mukta M Shukla; Amita M Shukla, all of 10423 Popkins Ct., Woodstock, MD (US) 21163

( * ) Notice: Subject to any disclaimer, the term of this patent is extended or adjusted under 35 U.S.C. 154(b) by 0 days.

(21) Appl. No.: 09/696,897

(22) Filed: Oct. 26, 2000

(51) Int. Cl.[7] .................... C12N 15/00; C12N 15/09; C12N 15/63; C12N 15/70; C02G 79/00
(52) U.S. Cl. ..................... 530/395; 435/6; 435/7.1; 435/320.1
(58) Field of Search ................. 435/6, 7.1, 320.1; 530/395

(56) References Cited

PUBLICATIONS

Martin Thurnher et al. Carbohydrate receptor–mediated gene trnasfer to human T leukaemic cells Glycobiology vol. No. 4 pp. 429–435, 1994.*

* cited by examiner

Primary Examiner—Andrew Wang
Assistant Examiner—Konstantina Katcheves

(57) ABSTRACT

In the present invention we describe a new method for the formation of a mucin-biomolecules complex, such as a mucin-DNA (deoxyribonucleic acid) complex and the application of such a complex for the transport of DNA, RNA (ribonucleic acid) and other biomolecules into cells. Transfection is the introduction of a DNA molecule into a eukaryotic cell, usually followed by the expression of one or more genes in the newly introduced DNA. The mucin-DNA complex described in the present invention can be used to perform transfection of DNA, as well as, the introduction of RNA and other larger biomolecules into cells. Since effective transfection, especially in in vivo systems is still limited by the methods currently available, the mucin-DNA complex, as described in the present invention, presents a novel and significantly improved method for performing transfection and ensuring the effective transmission of DNA into cells and the expression of genes in transfected DNA.

17 Claims, 5 Drawing Sheets

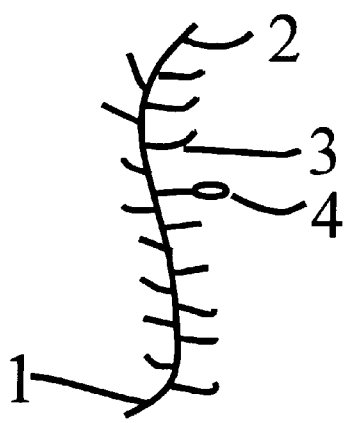
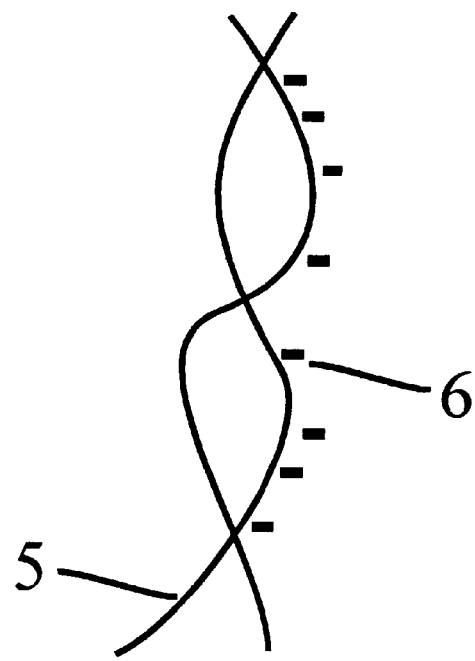
Fig. 1a  Fig. 1b

MUCIN-BIOMOLECULES COMPLEX FOR TRANSFECTION

FIELD OF THE INVENTION

In the present invention we describe a new method for the formation of a mucin-biomolecules complex, such as a mucin-DNA (deoxyribonucleic acid) complex and the application of such a complex for the transport of DNA, RNA (ribonucleic acid) and other biomolecules into cells. Transfection is the introduction of a DNA molecule into a eukaryotic cell, usually followed by the expression of one or more genes in the newly introduced DNA. The mucin-DNA complex described in the present invention can be used to perform transfection of DNA, as well as, the introduction of RNA and other larger biomolecules into cells. Since effective transfection, especially in in vivo systems is still limited by the methods currently available, the mucin-DNA complex, as described in the present invention, presents a novel and significantly improved method for performing transfection and ensuring the effective transmission of DNA into cells and the expression of genes in transfected DNA.

BACKGROUND OF THE INVENTION

Transfection, or the introduction of a DNA molecule into a eukaryotic cell, usually followed by the expression of one or more genes in the newly introduced DNA, represents one of the most important steps in genomics research and gene therapy. While methods for isolating DNA for transfection have improved significantly, effective methods for transfecting isolated DNA strands, especially in in vivo systems, are the limiting factor for progress in gene therapy. A number of transfection methods currently exist, yet each one of them is limited in the scope of its application and each presents certain disadvantages.

Current transfection methods include calcium phosphate precipitation, the use of a cationic lipid—DNA complex, electroporation and the use of viral vectors. Yet, calcium phosphate precipitation does not always yield high levels of transfection in cells. Cationic lipids, used in a complex, are often toxic to cells and thus ineffective for in vivo tranfection for gene therapy. Electroporation is a method where very high voltage levels are used to transport DNA into cells. Since DNA is highly negatively charged, the application of such an electric current allows for the passage of DNA into cells. Yet, this method cannot be used for in vivo transfection. Also, at high voltage levels the death rate of cells is significantly higher, even further limiting the scope of this method.

In viral vector transfection, the DNA to be tranfected is first introduced into the DNA of a virus. The virus, in turn, then injects its DNA, including the desired tranfection DNA, into a host cell. Although this method can be used in in vivo systems, one of its main disadvantages is that the virus can transform itself or its DNA and thus create undesirable side effects such as harmful infection of the host or undesired transformations to host DNA. The utility of this method is thus also significantly limited for gene therapy.

Since current transfection methods are so limited in their scope and utility there is strong need for a non-toxic method for in vivo transfection that has high success rates for transporting DNA into cells and that minimizes harmful side effects. Also, since the specificity of current methods is very limited, a more specific method for transfection is needed to ensure that desired DNA fragments are introduced into specific target cells. The present invention describes a mucin-DNA complex which represents a novel and highly effective method for transfection.

Mucins are glycoproteins with a very high molecular weight (usually more than 1 million Daltons). Mucins are generally about 60 percent or more carbohydrate by composition and water soluble. The carbohydrate molecules are generally attached as chains to the backbone of the proteins. Since carbohydrates are generally linear molecules the resulting structure can be likened to that of a comb, with the carbohydrate molecules forming individual prongs. When such a mucin molecule is combined with isolated strands of DNA a complex is formed in which the carbohydrate and protein molecules of mucin entangle the DNA strands to form a mucin-DNA complex. Said mucin-DNA complex can be precipitated using a number of different methods. Said complex can also be re-suspended and centrifuged to extract desired components of the complex.

SUMMARY OF THE INVENTION

The mucin-DNA complex as described in the present invention offers a number of advantages over currently available methods since said complex is:

1. non-toxic;
2. very specific since the choice of outer molecules on the mucin component of the complex can be used to specify which target cells will recognize said complex;
3. easy to create;
4. and, free of harmful side effects such as those resulting in cell toxicity.

Said mucin-DNA complex thus represents an effective method for transfection and thus presents a highly effective, new method for performing gene therapy.

The various features of novelty, which characterize the present invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawing, in which:

FIG. 1 is an expanded view of one embodiment of mucin (FIG. 1(a)) and DNA (FIG. 1(b)) molecules in chain form, according to the present invention.

DESCRIPTION OF THE PREFERRED EMBODIMENTS

Figure 2:
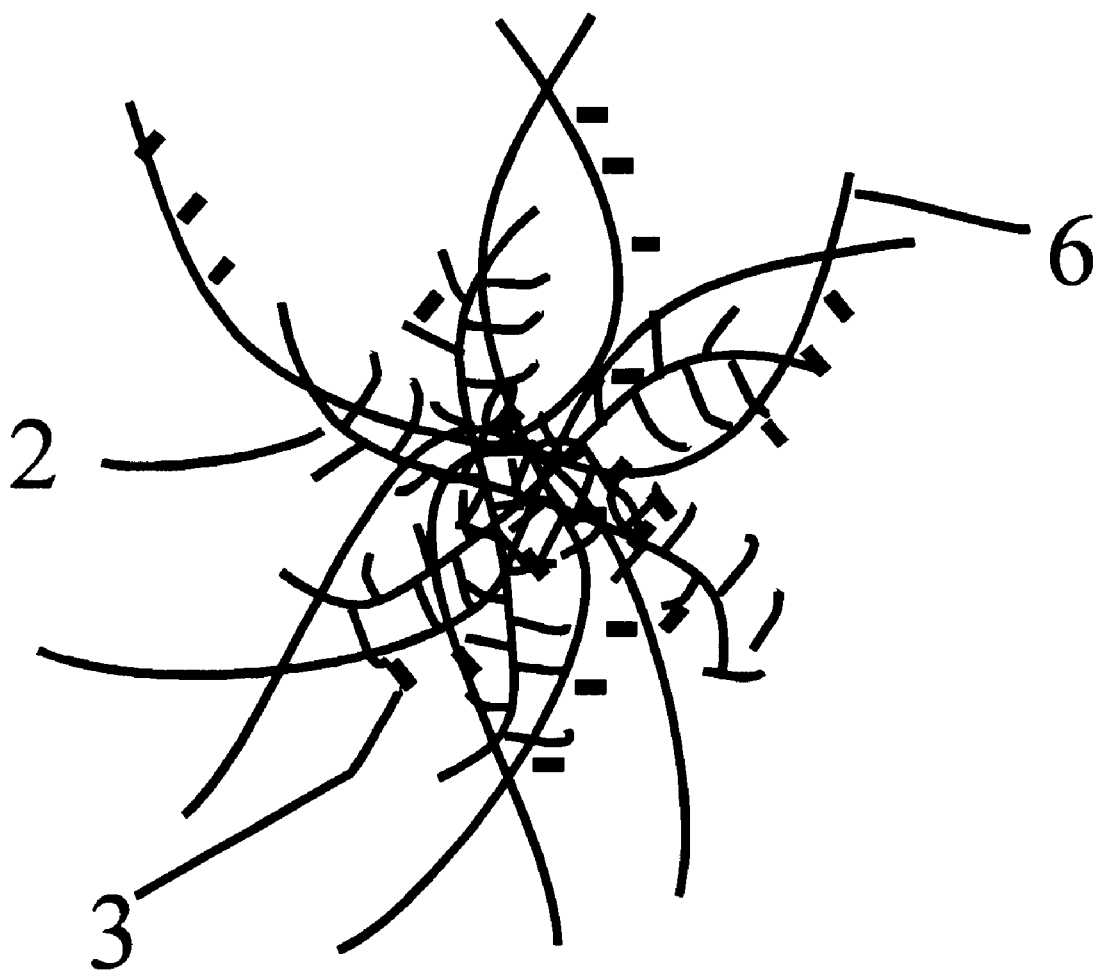
FIG. 2 is an expanded view of one embodiment of the mucin-DNA complex, according to the present invention.

FIG. 1(a) shows a mucin molecule (1) with a protein backbone (2) and carbohydrate chains (3) attached to said backbone (2). Said mucin molecule (1) may be any type of mucin molecule with a structure that may or may not resemble the structure and outline in FIG. 1(a). FIG. 1(b)

shows a linear representation of a DNA strand (5). As shown, the backbone of the DNA strand (6) contains negatively charged molecules.

FIG. 2 shows an entangled complex comprised of mucin and DNA molecules to form a mucin-DNA complex. As shown in FIG. 2, the protein backbone (2) and carbohydrate chains (3) of the mucin molecule are intertwined with the strands of the DNA molecule (5). When mucin and DNA are present in a complex as shown in FIG. 2, the individual strands of the respective molecules cannot be separated easily, creating the tangled complex shown in the figure. When a precipitating agent such as ethanol, tannins or an aqueous solution is used mucin and DNA both precipitate, forming a complex. The resulting mucin-DNA complex can be re-suspended in solution by agitation, shaking or ultrasonication, and can be re-precipitated again when centrifuged. Said mucin-DNA complex, as shown in FIG. 2, can be purified through centrifugation and washing with buffer.

The DNA strand (5) may be of any length and may be present in any configuration. Although FIG. 2 shows a DNA strand, the mucin molecule can also be used to form complexes with other biomolecules such as RNA, to form mucin-RNA complex or certain proteins to form mucin-protein complexes. In the latter example, RNA or said proteins are transported into a cell using the method of the present invention. The biomolecules bound to mucin may be any biomolecules from the group consisting of, but not limited to, DNA, RNA, nucleic acids, proteins, peptides, antibodies, glycolipid, glycoproteins, natural, synthetic and modified polymers, or any combination thereof.

Figure 3:
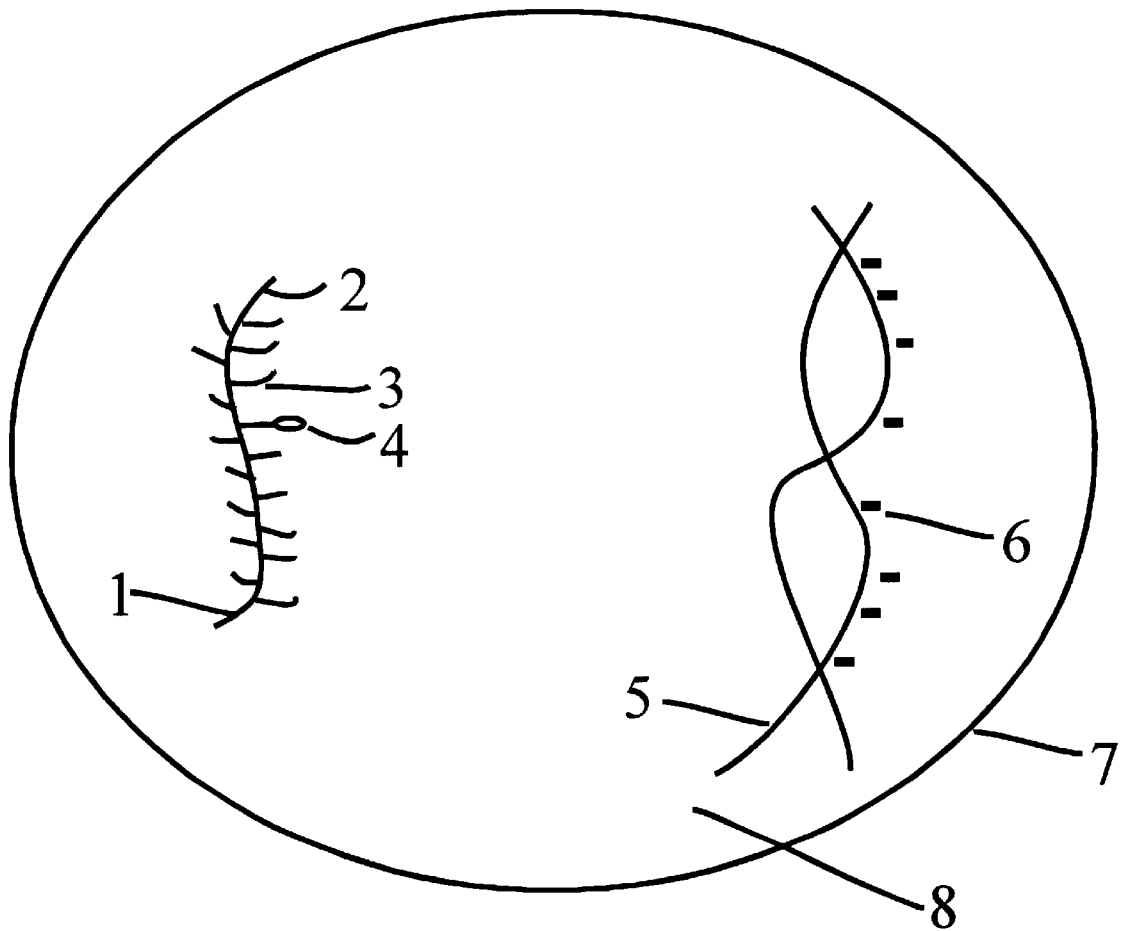
FIG. 3 is an expanded view of one embodiment of the mucin-DNA complex after transfection into a target cell, according to the present invention.

FIG. 3 shows a cell into which the mucin-DNA complex has been transported. Thus, the combination of DNA with mucin is effective for transporting strands of DNA (5) into desired target cells (7). As shown in FIG. 3, the mucin molecule components, the protein backbone (2) and complex carbohydrate strands (2) may break down into smaller particles upon entry into the interior of the cell (8), but the DNA strand (5) is transported intact, for the most part and results into the subsequent incorporation of the introduced DNA into the existing DNA of said cell (7).

Figure 4A:
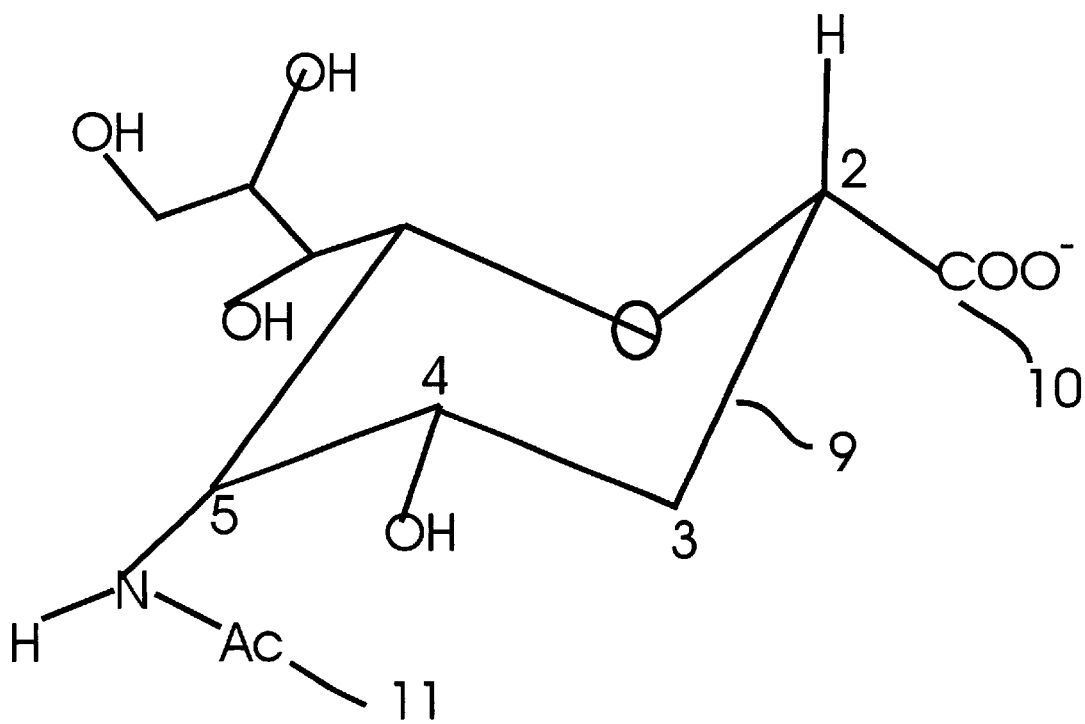
FIG. 4 is an expanded view of one embodiment of a molecule (sialic acid) from the carbohydrate chain of mucin with modification at the carboxyl group in FIG. 4(a) and modification at the N-acetyl group in FIG. 4(b), according to the present invention.
Figure 4B:
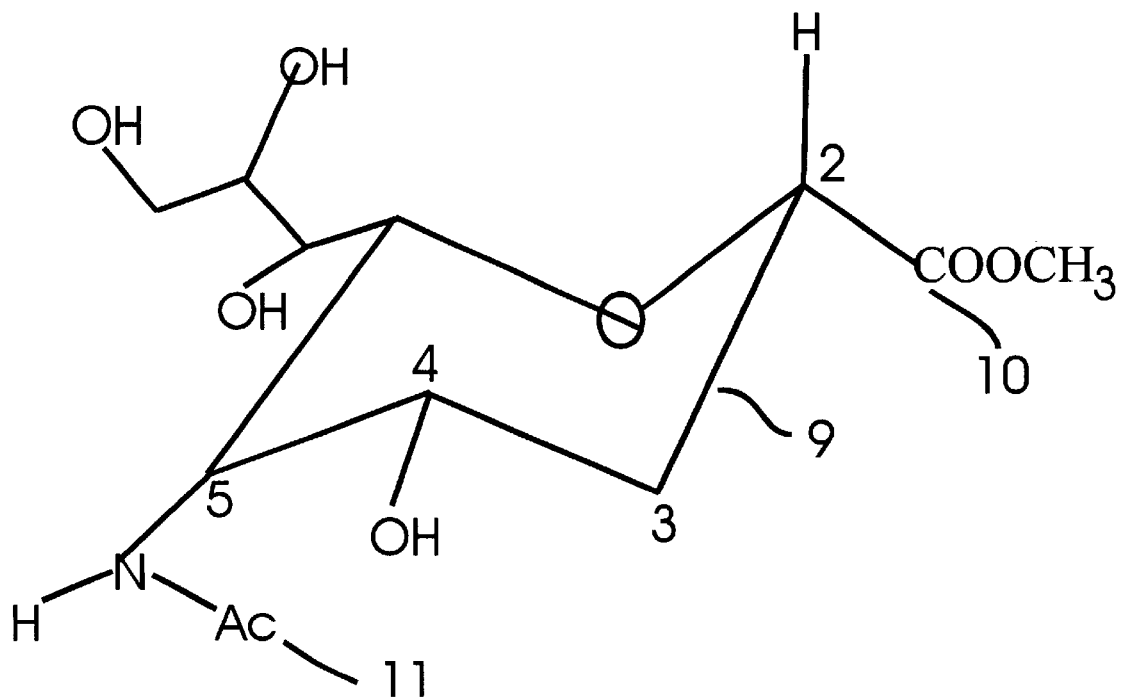

The specificity of target cells for transfection can be controlled through specific modifying molecules on the mucin component of the mucin-DNA complex, as shown in FIG. 4. FIG. 4(a) shows a carbohydrate molecule, sialic acid (9), where an ester group has been added to the carboxyl group (10), whereas FIG. 4(b) shows the same carbohydrate molecule (9) with modification at the N-acetyl group (11). Any type of modification can be performed on either the protein (2) or carbohydrate (3) components of said mucin molecule, as is relevant to a given set of cells targeted for transfection. Said modifications include the addition, removal or alternation or carbohydrate or protein components of mucin in said mucin-DNA complex.

One of the main advantages of the mucin-DNA complex, as shown in FIG. 2, is that mucin is a natural product and is non-toxic. For successful transfection for in vivo gene therapy mucin can be isolated from the same patient who will be the recipient of DNA during transfection. This is highly useful since it prevents the risk of toxicity to the patient. Also, as shown in FIG. 3, mucin can be chemically modified. Furthermore, mucin can also be used in natural or chemical form and can be purified or modified using any chemical or enzymatic methods.

Mammalian organisms and cells represent a significant source of mucin, but any other organisms or cells, including bacteria or plants can also be used as mucin sources. Once mucin is obtained from a desired source it can be purified by chromatographic methods or by precipitation and re-suspension. Alternately, mucin can also be used in 'as-is' form from the source, without further purification.

Most mammalian mucin molecules have sialic acids as terminal molecules. The total or partial removal of sialic acid molecules, either enzymatically or chemically, can further enhance the binding of DNA to the mucin. Since both DNA and sialic acids are highly negatively charged, the two types of molecules would repel each other. With the removal of sialic acid, DNA binds to mucin more easily. Furthermore, the removal of sialic acid also enhances the endocytosis of the mucin-DNA complex. Endocytosis is the process whereby a cell adheres a certain molecule or complex to its exterior cell membrane and then engulfs it to introduce that molecule or complex into the interior of the cell. When sialic acid is removed from mucin, galactose molecules become the terminal molecules of the mucin carbohydrate chains. Galactose is often better recognized by cell surface molecules for endocytosis of the mucin-DNA complex.

Thus, modifications, such as the removal of sialic acid, may be advantageous and could be performed on the native mucin to enhance its transfection capabilities. Alternately, the negative charges on sialic acid could be suppressed by the esterfication (addition of an ester group) to the carboxyl group (10) of sialic acid (9), as shown in FIG. 4(b). The subsequent formation of an ester group (ethyl or methyl) would remove the negative charge from sialic acid. Furthermore, sialic acid has an N-acetyl group at C-5 (11), as shown in FIG. 4(a). The removal of this acetyl group would confer a positive charge on that component of the sialic acid molecule, thus increasing its binding to the negatively charged DNA. Alternately, both the acetyl group and the hydrogen atom at the nitrogen atom can be replaced with alkyl groups, such as $—CH_3$, $—C_2H_5$. Either one or both of these modifications can be performed on sialic acid to enhance the binding of DNA to mucin to form said mucin-DNA complex.

Furthermore, specific exoglycosidases can be used to expose specific carbohydrate groups on the mucin carbohydrate chains. This method can be used to tailor the properties of the mucin-DNA complex to the receptors present on specific target cells and to thus enhance endocytosis and transfection. For examples, lung cells recognize mannose in the terminal position whereas the liver's Kuffer cells recognize galactose in the terminal position. Still other cells may have sialic acid binding protein receptors (sialolectins).

The mucin used to form said mucin-DNA complex can consist of one or more different types of mucin molecules, each with the same or different types of modifications. The mucin-DNA complex, as described in the present invention thus offers a new tool for the transfection of cells and for the in vivo, or in vitro, delivery of DNA, RNA and other biomolecules into cells. The present invention can thus be used for gene therapy, for cell repair, cell modification or for the production of specific proteins or enzymes in specific cells. Said mucin-DNA complex is not limited by the size of DNA or other biomolecules used to form the complex with mucin.

The broader usefulness of the present invention may be illustrated by the following examples.

EXAMPLE 1

Formation of a Mucin-DNA Complex

Fluorescence tagged DNA was added to a mucin solution and the mixture was agitated by the use of a vortex for 1–2 minutes. The mucin was precipitated by the addition of isopropanol or other organic solvents. The resulting precipitate showed fluorescence whereas the remaining solution showed no fluorescence.

EXAMPLE 2

Stress Induction on a Newly Formed Mucin-DNA Complex

Fluorescence tagged DNA was added to a mucin solution and the mixture was agitated by the use of a vortex for 1–2 minutes. The mucin was precipitated by the addition of a gallnut extract, a natural product which has mucin precipitating properties. After precipitation the mucin-DNA complex showed fluorescence while the remaining solution showed no fluorescence, indicating that all of the DNA had combined with the mucin to form a mucin-DNA complex. The mucin-DNA complex was re-suspended in water and centrifuged for 1–2 minutes. Again, only the mucin-DNA complex showed fluorescence while the supernatant showed no fluorescence. Thus, the mucin-DNA complex formed, according to the present invention, is highly stable.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A mucin-DNA (deoxyribonucleic acid) complex formed by combining mucin and DNA wherein the complex is capable of transport into a cell.

2. A mucin-biomolecules complex formed by combining mucin and biomolecules wherein the complex is capable of transport into a cell.

3. The mucin-DNA complex of claim 1, where said mucin is selected from the group consisting of mucin from a biological source, mucin from a non-biological source and combinations thereof.

4. The mucin-DNA complex of claim 1, where said mucin is selected from the group consisting of mucin in its native state, biologically modified mucin, chemically modified mucin, mucin modified by enzymes, mucin modified by heat-based methods and combinations thereof.

5. The mucin-DNA complex of claim 1, where said mucin contains sialic acid.

6. The mucin-DNA complex of claim 1, where said DNA is selected from the group consisting of DNA in its natural state, modified DNA, synthetically created DNA, linear DNA, circular DNA, single-stranded DNA, double-stranded DNA and combinations thereof.

7. The mucin-DNA complex of claim 1, where said complex is purified by a method selected from the group consisting of chromatographic methods, centrifugation methods and, combinations thereof.

8. The mucin-DNA complex of claim 1, where said mucin in said complex is modified by the addition, removal or alteration of a carbohydrate or a protein component of said mucin.

9. A mucin-DNA complex as in claim 1, where said mucin in said complex is modified to target specific cells as the targets of transfection.

10. A mucin-biomolecules complex as in claim 2, where said biomolecules are selected from the group consisting of DNA, RNA, nucleic acids, proteins, peptides, antibodies, glycolipids, glycoproteins, natural polymers, synthetic polymers, modified polymers, and combinations thereof.

11. The mucin-biomolecules complex of claim 2, where said biomolecules is selected from the group consisting of biomolecules in its natural state, modified biomolecules, synthetically created biomolecules and combinations thereof.

12. The mucin-DNA complex of claim 2, where said mucin is selected from the group consisting of mucin from a biological source; mucin from a non-biological source; and, combinations thereof.

13. The mucin-DNA complex of claim 2, where said mucin is selected from the group consisting of mucin in its native state; biologically modified mucin; chemically modified mucin; mucin modified by enzymes; mucin modified by heat-based methods; and, combinations thereof.

14. The mucin-DNA complex of claim 2, where said mucin contains sialic acid.

15. The mucin-DNA complex of claim 2, where said complex is purified by a method selected from the group consisting of chromatographic methods, centrifugation methods, and, combinations thereof.

16. The mucin-biomolecules complex of claim 2, where said complex the addition, removal or alteration of a carbohydrate or a protein component of said mucin.

17. The mucin-DNA complex of claim 2, where said mucin in said complex is modified to target specific cells as the targets of transfection.

\* \* \* \* \*

UNITED STATES PATENT AND TRADEMARK OFFICE
CERTIFICATE OF CORRECTION

PATENT NO. : 6,320,030 B1
APPLICATION NO. : 09/696897
DATED : November 20, 2001
INVENTOR(S) : Ashok K. Shukla, Mukta M. Shukla and Amita M. Shukla It is certified that error appears in the above-identified patent and that said Letters Patent is hereby corrected as shown below:

In claim 14, 15, 16, 17

"The mucin-DNA complex of claim 2"

Should be replaced by

-- The mucin-biomolecule complex of claim 2 --

Signed and Sealed this

Twenty-second Day of January, 2008

JON W. DUDAS
*Director of the United States Patent and Trademark Office*